United States Patent [19]

Durham et al.

[11] Patent Number: 5,693,054
[45] Date of Patent: Dec. 2, 1997

[54] DEVICE AND METHOD FOR REDUCING FRACTURES IN LONG BONES

[76] Inventors: Alfred A. Durham; Dallas P. Crickenberger, both of 2110 Carolina Ave., SW, Roanoke, Va. 24014

[21] Appl. No.: 237,923

[22] Filed: May 4, 1994

[51] Int. Cl.⁶ .................................................. A61B 17/72
[52] U.S. Cl. ........................... 606/62; 606/86; 606/102
[58] Field of Search ............................ 606/62, 64, 67, 606/72, 75, 76, 104, 205, 208, 60, 96, 86, 102; 128/898; 33/511, 512, 645, 533, DIG. 1

[56] References Cited

U.S. PATENT DOCUMENTS

| | | |
|---|---|---|
| 3,961,632 | 6/1976 | Mossun . |
| 4,570,624 | 2/1986 | Wu . |
| 4,621,628 | 11/1986 | Brudermann . |
| 4,803,976 | 2/1989 | Frigg et al. . |
| 4,850,344 | 7/1989 | Olerud et al. . |
| 4,865,025 | 9/1989 | Buzzi et al. . |
| 4,877,019 | 10/1989 | Vives . |
| 4,881,535 | 11/1989 | Sohngen ........................ 606/98 |
| 4,901,711 | 2/1990 | Goble et al. .................... 606/98 |
| 4,917,111 | 4/1990 | Pennig et al. .................. 606/97 |
| 4,969,889 | 11/1990 | Greig ............................ 606/97 |
| 5,013,317 | 5/1991 | Cole et al. ..................... 606/96 |
| 5,049,151 | 9/1991 | Durham et al. ................. 606/98 |
| 5,127,913 | 7/1992 | Thomas, Jr. ................... 606/62 |

FOREIGN PATENT DOCUMENTS

| | | |
|---|---|---|
| 221356 | 4/1985 | Germany . |
| 668692 | 1/1989 | Switzerland . |
| 1447351 | 12/1988 | U.S.S.R. . |

OTHER PUBLICATIONS

Chaltos, William F., "Measurement of the Prostate in vivo with Magnetic Fields", 12 Sep. 1963.

*Primary Examiner*—Guy V. Tucker
*Attorney, Agent, or Firm*—Larson and Taylor

[57] ABSTRACT

Reduction of a fracture in a long bone is provided by a magnetic reducing rod assembly including a pair of reducing rod devices each comprising a flexible rod having a magnet at one end thereof. The magnets on the rods are inserted into the bone at opposite ends thereof and are caused to move along the bone until the magnets are brought into collinear alignment wherein the associated rods provide reduction of the fracture. An audio sensing system assists in aligning the magnets by producing a sound which varies in relation to the proximity of the magnets. The reducing rod devices are ultimately removed and replaced by a conventional intramedullary rod.

22 Claims, 4 Drawing Sheets

DEVICE AND METHOD FOR REDUCING FRACTURES IN LONG BONES

FIELD OF THE INVENTION

The present invention relates to the alignment of long bone fractures and, more particularly, to a magnetic device for reducing such fractures, i.e., for correcting the fracture by bringing displaced or broken parts back into their normal positions, and to a method of using the device.

BACKGROUND OF THE INVENTION

Fractures of the long bones such as the femur frequently do not exactly align when the bones are being prepared for surgery. Most commonly, this lack of alignment is overcome by using an intramedullary rod or "nail" which is inserted into the intramedullary canal of the bone to stabilize the fracture. The task of reducing the fracture is often the most time consuming step involved in the operation and, in this regard, the time required can vary from minutes to hours. The reduction is frequently carried out using a intramedullary rod in the form of a bent "reducing rod" and the procedure typically requires long X-ray exposures.

Patents of interest in this general field include our earlier patent, U.S. Pat. No. 5,049,151 (Durham et al.) which discloses a magnetic positioner arrangement for locking screws for orthopedic hardware such as intramedullary "nails." Other patents of interest include U.S. Pat. Nos. 4,621,628 (Brudermann); 4,625,718 (Olerud et la.); and 4,570,624 (Wu). The Brudermann patent discloses an apparatus for locating transverse holes in the distal ends of implanted intramedullary locking "nails." In general, the Durham et al. and Brudermann patents are concerned with positioning of locking screws after the "nail" is in place and not with the placement or positioning of the "nail" itself.

SUMMARY OF THE INVENTION

In accordance with the invention, a device is provided which enables the fracture to be reduced magnetically, thereby eliminating the need for x-ray exposure or reducing such exposures to a minimum.

In accordance with one aspect of the invention, a magnetic reduction assembly is provided for assisting in reducing fractures in long bones, the assembly comprising first and second magnetic reducing rod devices each comprising an elongate rod member for insertion longitudinally at one end thereof into a bone to be reduced, and a permanent magnet located at said one end of the rod member, the magnets of the reducing rod devices being of opposite polarity.

During use, the rod members are inserted into opposite ends of a bone to be reduced, and the assembly preferably further comprises indicator means for, during use of the reducing rod devices, indicating the proximity of the magnets of the rod members to one another. Advantageously, the indicator means includes detector means for sensing a parameter related to the proximity of the magnets and for producing a corresponding output signal, and a signaling means for receiving said output signal and for producing an output related thereto. The signaling means preferably comprises an audio amplifier for converting the output signal from the detector means into an audio sound. In one preferred embodiment, the detector means comprises a strain gauge. In another preferred embodiment, the detector means comprises a pick-up coil wrapped around an associated magnet.

In a preferred embodiment, the magnetic reducing rod devices each further comprises a housing for the associated magnet. Advantageously, each housing comprises protective shell formed by thin walls fabricated of a metal such as a stainless steel. The permanent magnets are preferably very strong magnets and, in an advantageous implementation, each comprises a neodymium iron boron magnet.

The rod members of the reducing rod devices each preferably comprise a flexible rod. In a preferred embodiment, the flexible rod comprises a spiral coil spring. In a preferred implementation, the detector means mentioned above comprises first and second detectors each respectively associated with one of the magnets and housed in a protective housing with the associated magnet, and each coil spring of the reducing rod devices includes a central cannulation through which output leads of the detectors extend so as to provide an electrical connection to an external signaling or indicator device such as the above-mentioned audio amplifier employed in a preferred embodiment.

In accordance with a further aspect of the invention, a method is provided for reducing a fracture in a long bone using first and second magnetic reducing rods each comprising a rod member and a magnet located at one end of said rod member, the method comprising: inserting the magnets of first and second magnetic reducing rods into opposite ends of a long bone to be reduced and moving said rods longitudinally within the intramedullary canal of the bone until said magnets are brought into collinear alignment; inserting an exchange tube into one end of the bone over the rod member at that end and to a depth beyond the fracture site; pulling the magnets apart within the exchange tube and removing the magnets and associated rod members from the bone at opposite ends of the bone; inserting a guide wire into the exchange tube and along the intramedullary canal of the bone; removing the exchange tube; inserting an intramedullary rod over the guide wire into the intramedullary canal so that the intramedullary rod extends along the length of the bone; and fixing the intramedullary rod in place in the bone.

Preferably, the method further comprises using detectors mounted on the rod members along with the magnets to determine the proximity of the magnets to one another and to enable the magnets to be brought into alignment. Advantageously, the method also includes using an audio amplifier connected to the detectors to produce an audio signal indicative of the proximity of the magnets so as to assist in the alignment of the magnets.

Other features and advantages of the invention will be set forth in, or apparent from, the following detailed description of preferred embodiments of the invention.

DESCRIPTION OF THE PREFERRED EMBODIMENTS

Figure 1:
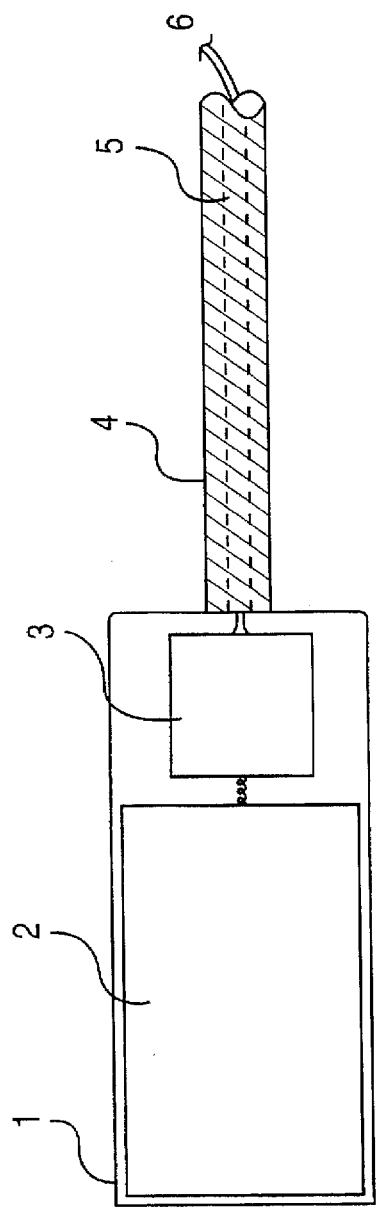
FIG. 1 is a schematic cross sectional view of a magnetic reducing rod in accordance with a first embodiment of the invention.

Referring to FIG. 1, a first embodiment of one magnet unit or device of the magnetic reduction system of the invention is shown. As explained below in connection with FIGS. 3 and 4, the overall system includes a second magnet unit (including a magnet of the opposite polarity) as well as a detector arrangement. The embodiment of FIG. 1 includes a thin walled housing or protective covering 1 preferably made of stainless steel, titanium or the like, which encloses a permanent magnet 2. Magnet 2 is a strong magnet and is preferably of a conventional neodymium iron born type. A small strain gauge, indicated at 3, is attached to magnet 2 so as to measure the forces exerted therein. A hollow spiral core spring 4, having a central bore or cannulation 5 therein and forming a flexible rod, is affixed to housing 1. Suitable output conductors or wire leads 6 extend from strain gauge 3 through central cannulation 5 so as to permit connection thereof to suitable metering described below.

Figure 2:
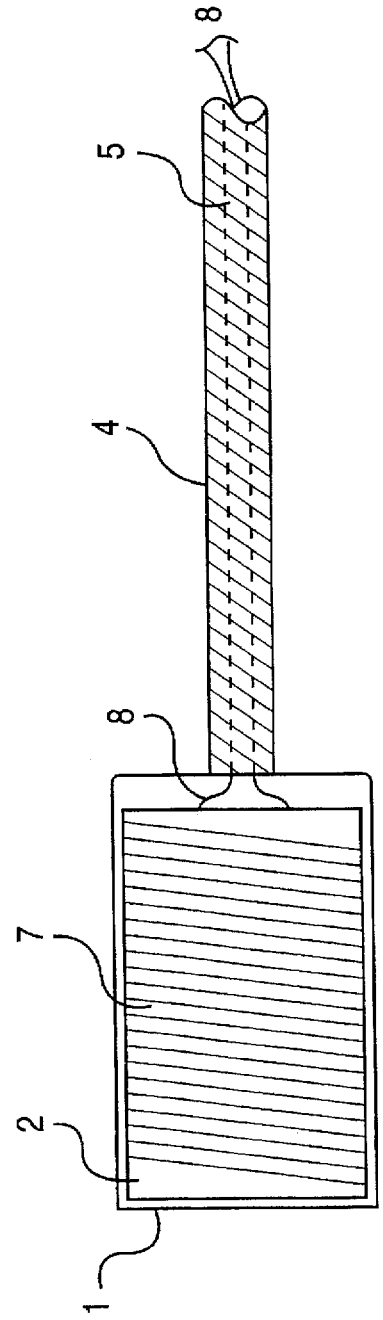
FIG. 2 is a schematic cross sectional view of a magnetic reducing rod in accordance with a second embodiment of the invention.

Referring to FIG. 2, a second embodiment of the magnet unit is shown. This embodiment is similar to that of FIG. 1 and includes a corresponding housing 1, magnet 2 and spiral spring rod 4 with an inner cannulation 5, but instead of strain gauge 3 uses a reference conductor or wire coil 7 wrapped around magnet 2 and having output leads 8 which pass through the bore core or cannulation 5 in spring 4 in a similar manner to wire 6 of FIG. 1. Although separate embodiments are illustrated (and other variations are, of course, possible within the scope and spirit of the invention), the two illustrated embodiments operate in a similar manner to produce a similar output signal and will not be considered separately in the discussion of the overall operation of the system of the invention which follows.

Figure 3:
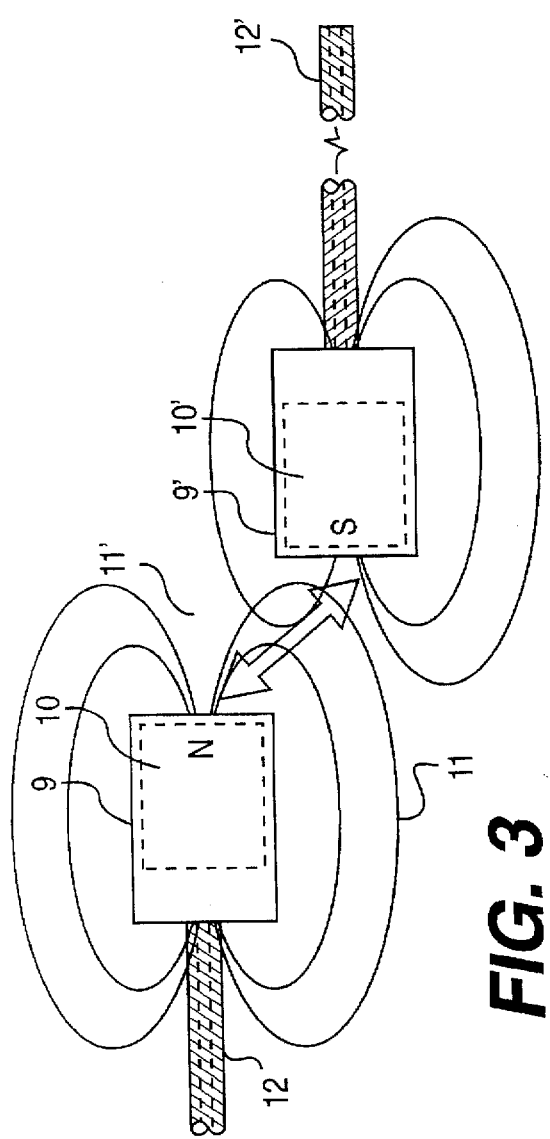
FIG. 3 is a schematic side elevational view of two magnetic reducing rods, showing the interaction between the magnetic fields of force.
Figure 4:
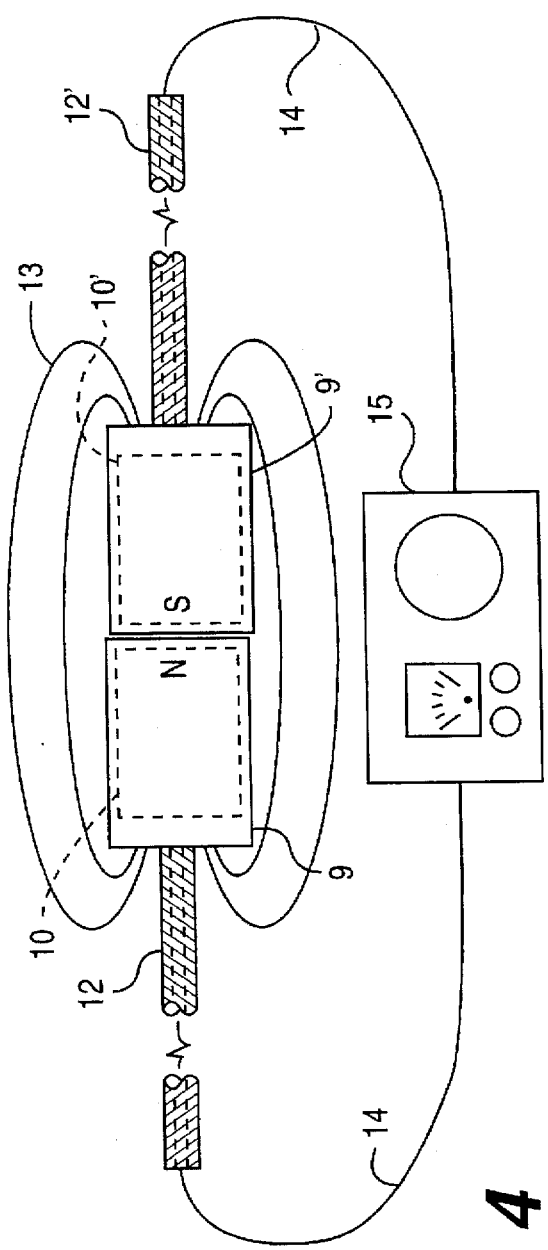
FIG. 4 is a schematic side elevational view of the overall system of the invention and showing the reducing rods in alignment.

Referring to FIGS. 3 and 4, the basic operating principles of the system of the invention are illustrated. FIG. 3 shows two magnet units 9 and 9' which house magnets 10 and 10' of opposite polarity and which are connected to respective spiral spring rods 12 and 12'. Magnets 10 and 10' create respective flux fields 11 and 11' which produce a mutually attractive forces indicated by arrow A, and tend to line up, i.e., come into alignment or become collinear, in accordance with the laws of magnetism. This collinear alignment of the magnets 10 and 10' is shown in FIG. 4 in which the resultant flux field, indicated at 13, is shown as now enveloping both magnets 10 and 10'. The output conductors 14 and 14' of the two units 9 and 9' (corresponding to the leads 6 from strain gauge 3 of FIG. 1 or the leads 8 from coil 7 of FIG. 2) are connected to an audio amplifier 15 at which the output signal is converted into an audio sound. The purpose of audio amplifier 15 is to assist an operator in gauging the proximity of the magnets 9 and 9' to each other as they move relative to one another. As explained above, an alignment or reduction procedure would ordinarily be performed under X-ray control using relatively long X-ray exposures.

Figure 7:
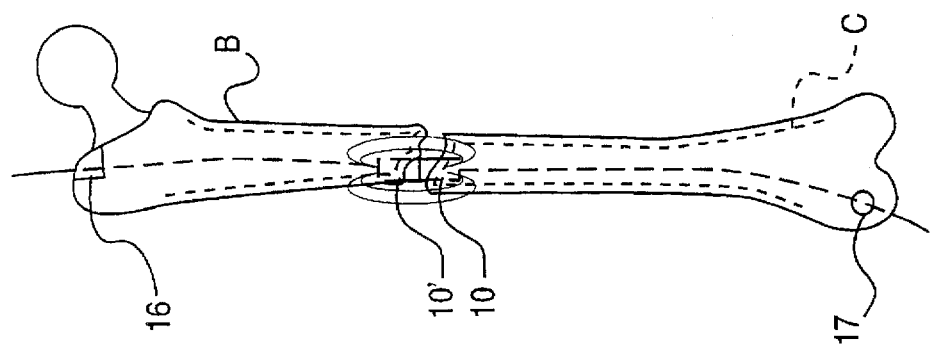
FIGS. 5 to 10 illustrate steps in the method of the invention showing the use of the magnetic reducing rods in assisting in providing reduction of a fracture in a long bone.
Figure 6:
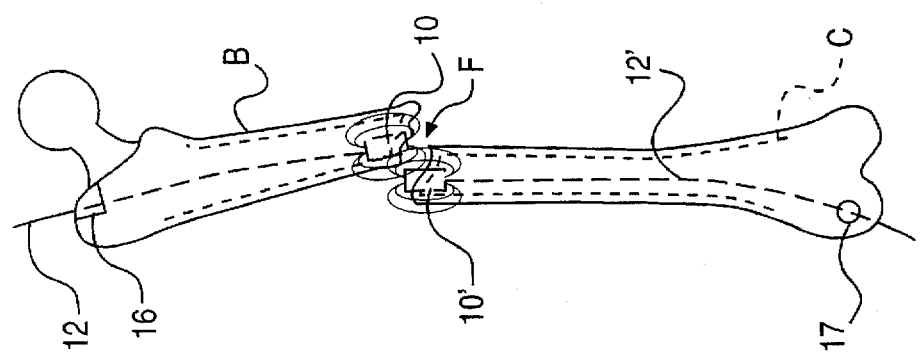
Figure 5:
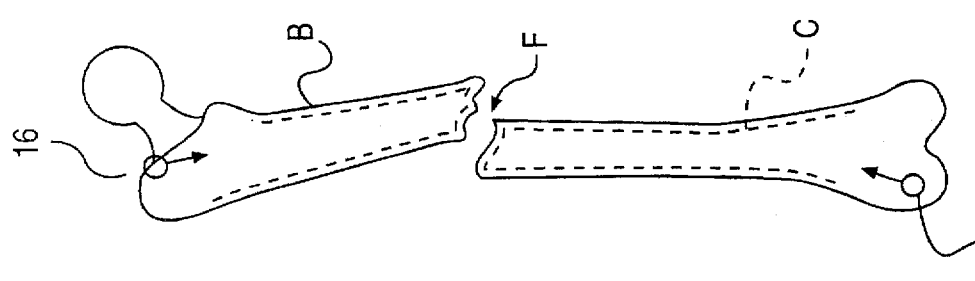

Referring to FIGS. 5 to 10, there are illustrated, in a schematic manner, successive steps in the method of use of the magnetic reduction system of the invention in reducing a long bone, denoted B, such as a femur. As shown in FIG. 5, bone B has a fracture F therein (and the bone is not reduced) and entry points 16 and 17 are provided, e.g., by drilling into the bone, at opposite ends thereof. As shown in FIG. 6, these entry points 16 and 17 enable spiral spring rods 12 and 12', corresponding to those of FIGS. 3 and 4 and having magnet units 10 and 10' at the distal ends thereof, to be inserted into the intramedullary canal of bone B. The intramedullary canal is indicated in dashed lines at C in FIGS. 5 and 16. The rods 12 and 12' are pushed into this internal canal from opposite ends thereof so that magnet units 10 and 10' are disposed at the fracture site and thus the respective magnetic fields of the units interact. As shown in FIG. 7, as the magnets of units 10 and 10' couple together and align, the fracture is reduced.

Considering the magnet alignment process in more detail and referring again to the system shown in FIG. 4 as implemented in accordance with the embodiment of FIG. 1, as two magnets of units 10 and 10' are introduced from opposite ends of the bone B and come into close enough proximity that the magnetic fields interact, the strain gauges of the units (corresponding to strain gauge 3 of FIG. 1) measure the attractive forces exerted by the magnets and produce a corresponding electrical signal which is converted into an audio signal by amplifier unit 15. The closer the magnets come together the louder the audio signal that is produced. When the magnet unit 10 and 10' actually make contact, a series circuit is completed which includes amplifier unit 15 and a second audio signal, different from the first signal, is produced by amplifier unit 15, thereby indicating by the unique sound associated with the second audio signal that the magnets are in contact at the fracture site.

Figure 8:
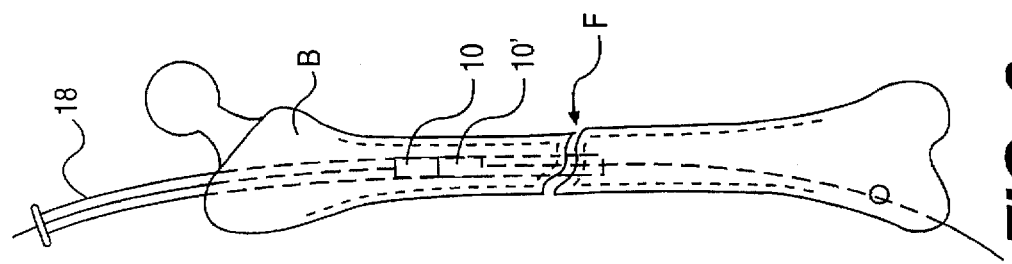

Referring to FIG. 8, further steps in the overall method or process is shown, as a first step, the bottom magnet unit 10' is pushed proximally (upwardly in FIG. 8) and the top magnet unit 10 is simultaneously pulled or retracted so that the coupled units 10 and 10' are withdrawn into the proximal fragment of bone B. When this is done, an exchange tube 18 is passed over the rods 12 and 12' and associated coupled magnet units 10 and 10'. Once exchange tube 18 is inserted to a depth beyond the fracture F (as is shown in FIG. 8), magnet units 10 and 10' can be separated from each other and removed with their corresponding spiral spring rods from the respective ends of bone B through holes 16 and 17.

Figure 9:
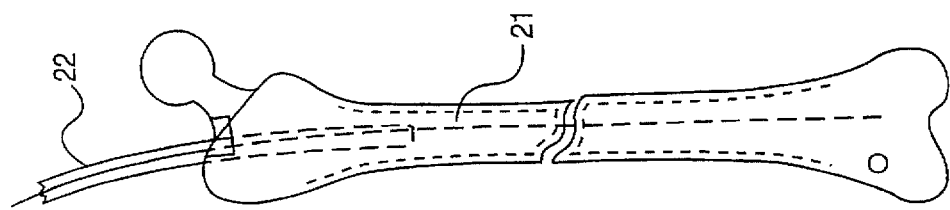

Referring to FIG. 9, removal of units 10 and 10' enables a guide wire 21 to then be inserted through the exchange tube 18 (not shown in FIG. 9) into the intramedullary canal. The insertion of guide wire 21 into place ultimately enables an intramedullary rod 22 to be put into place in the intramedullary canal C.

Figure 10:
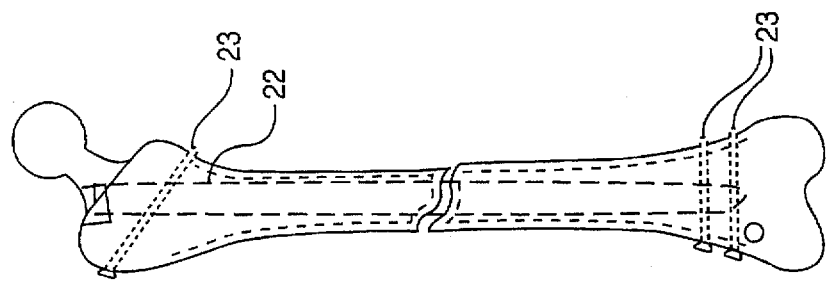

FIG. 10 shows intramedullary rod 21 fully positioned within bone B and the use of cross locking screws 22 to fix rod 21 in place.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A magnetic reduction assembly for assisting in reducing fractures in long bones, said assembly comprising first and second magnetic reducing rod devices each comprising an elongate rod member for insertion longitudinally at one end thereof into a bone to be reduced, and a permanent magnet support portion located at said one end of said rod member and supporting a permanent magnet, the magnets of said reducing rod devices being of opposite polarity, at least one of said rod members comprising a flexible rod of substantially greater axial flexibility per unit length than the magnet and the permanent magnet support portion of said at least one rod member.

2. An assembly as claimed in claim 1 wherein, during use, said rod members are inserted into opposite ends of a bone to be reduced, said assembly further comprising indicator means for, during use of said reducing rod devices, indicating the proximity of said magnets of said rod members to one another.

3. An assembly as claimed in claim 2 wherein said indicator means includes detector means for sensing a parameter related to the proximity of said magnets and for producing a corresponding output signal, and a signaling means for receiving said output signal and for producing an output related thereto.

4. An assembly as claimed in claim 3 wherein said signaling means comprises an audio amplifier for converting said output signal into an audio sound.

5. An assembly as claimed in claim 2 wherein said detector means comprises a strain gauge.

6. An assembly as claimed in claim 2 wherein said detector means comprises a pick-up coil wrapped around an associated magnet.

7. A magnetic reduction assembly as claimed in claim 1 wherein said magnetic reducing rod devices each further comprises a housing for the associated magnet.

8. An assembly as claimed in claim 7 wherein said housing comprises protective shell formed by thin walls fabricated of a metal.

9. An assembly as claimed in claim 8 wherein said walls of said housing are comprised of a stainless steel.

10. An assembly as claimed in claim 1 wherein said permanent magnets each comprise a neodymium iron boron magnet.

11. An assembly as claimed in claim 1 wherein each of said rod members comprises a flexible rod.

12. An assembly as claimed in claim 11 wherein each of said flexible rods comprises a spiral coil spring.

13. An assembly as claimed in claim 12 wherein said assembly further comprises indicator means for, during use of said reducing rod devices, indicating the proximity of said magnets, said indicator means including an external signaling device, a first detector associated with one of said permanent magnets and a second detector associated with the other of said permanent magnets, said detectors being housed in a protective housing with the associated magnet, each coil spring of said reducing rod devices including a central cannulation and said detectors including output leads extending through the cannulation in the associated coil spring and connected to said signaling device.

14. A magnetic reducing rod system for use in reducing fractures of long bones, said system comprising first and second reducing rod devices for insertion into opposite ends of a long bone having a fracture to be reduced, and indicating means for indicating the proximity of said rods to one another, each said reducing rod device comprising a rod member, a magnet located at one end of the rod member, a protective housing for said magnet disposed at said one end of said rod member, and a detector located within said housing for detecting the proximity of said magnet to the magnet of the other reducing rod device, and said indicating means including a signaling device responsive to said detectors for producing an output indicative of the proximity of the magnets of the first and second reducing rod devices so as to assist providing collinear alignment of said magnets within the bone, at least one of said rod members comprising a flexible rod of substantially greater flexibility per unit length than the magnet and protective housing of said at least one rod member.

15. A system as claimed in claim 14 wherein said signaling device comprises an audio device for producing an audio sound having an intensity proportional to the proximity of said magnets.

16. A system as claimed in claim 15 wherein said audio device comprises an audio amplifier for producing a further audio sound when said magnets are in alignment.

17. A system as claimed in claim 14 wherein the rod members of said reducing rod devices each comprise a flexible spiral elongate spring member.

18. A system as claimed in claim 17 wherein each said spring member includes an inner cannulation and said system further includes electrical connections extending through the cannulations in the spring members of the first and second rod devices for interconnecting the detectors of the devices to the signaling device.

19. A method for reducing a fracture in a long bone using first and second magnetic reducing rods each comprising a rod member and a magnet located at one end of said rod member, said method comprising inserting the magnets of first and second magnetic reducing rods into opposite ends of a long bone to be reduced and moving said rods longitudinally within the intramedullary canal of the bone until said magnets are brought into collinear alignment, inserting an exchange tube into one end of the bone over the rod member at that end and to a depth beyond the fracture site, pulling the magnets apart within said exchange tube and removing the magnets and associated rod members from the bone, inserting a guide wire into the exchange tube and along the intramedullary canal of the bone; removing the exchange tube; inserting an intramedullary rod over said guide wire into the intramedullary canal so that the intramedullary rod extends along the length of the bone; and fixing the intramedullary rod in place.

20. A method as claimed in claim 19 wherein the step of moving said rods further comprises determining the proximity of said magnets using detectors mounted on the rod members along with the magnets to determine the proximity of the magnets to one another and to bring the magnets into alignment.

21. A method as claimed in claim 20 wherein the step determining the proximity of the magnets further comprises using an audio amplifier connected to said detectors to produce an audio signal indicative of the proximity of the magnets so as to assist in the alignment of the magnets.

22. A magnetic reduction assembly for assisting in reducing fractures in long bones, said assembly comprising first and second magnetic reducing rod devices each comprising an elongate rod member for insertion longitudinally at one end thereof into a bone to be reduced, and a permanent magnet support portion located at said one end of said rod member and supporting a permanent magnet, said rod numbers, during use, being inserted into opposite ends of a bone to be reduced, and said assembly further comprising indicator means, for during use of said reducing rod devices, indicating the proximity of said magnets of said rod members to one another.

* * * * *